(12) United States Patent
Chabin et al.

(10) Patent No.: US 11,074,688 B2
(45) Date of Patent: Jul. 27, 2021

(54) DETERMINATION OF A DEGREE OF DEFORMITY OF AT LEAST ONE VERTEBRAL BONE

(71) Applicant: Siemens Healthcare GmbH, Erlangen (DE)

(72) Inventors: Guillaume Chabin, Princeton, NJ (US); Jonathan Sperl, Bamberg (DE); Rainer Kärgel, Forchheim (DE); Sasa Grbic, Plainsboro, NJ (US); Razvan Ionasec, Nuremberg (DE); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 40 days.

(21) Appl. No.: 16/678,046

(22) Filed: Nov. 8, 2019

(65) Prior Publication Data

US 2020/0160515 A1    May 21, 2020

(30) Foreign Application Priority Data

Nov. 21, 2018  (EP) .................................... 18207641

(51) Int. Cl.
*G06T 7/73* (2017.01)
*A61B 5/00* (2006.01)
*G06T 7/00* (2017.01)

(52) U.S. Cl.
CPC .......... *G06T 7/0012* (2013.01); *A61B 5/4509* (2013.01); *G06T 7/73* (2017.01); *G06T 2207/30012* (2013.01)

(58) Field of Classification Search
CPC .................. G06T 7/0012; G06T 7/73; G06T 2207/30012; G06T 2207/10072; G06T 7/11; A61B 5/4509; A61B 6/5217; A61B 6/505; G06K 2209/055; G06K 9/627; G06K 9/4638; G06K 9/2018; G06N 3/0454; G06N 3/08
See application file for complete search history.

(56) References Cited

U.S. PATENT DOCUMENTS

| 2009/0297012 A1 | 12/2009 | Brett et al. |
| 2011/0142307 A1 | 6/2011 | Ghosh et al. |
| 2014/0323845 A1* | 10/2014 | Forsberg ............. A61B 5/4561 600/407 |
| 2017/0178349 A1* | 6/2017 | Ketcha ...................... G06T 7/33 |

(Continued)

OTHER PUBLICATIONS

Xinghu Yu, Chao Ye, Liangbi Xiang: "Application of Artificial Neural Network in the Diagnostic System of Osteoporosis" Jun. 15, 2016, Neurocomputing 214 (2016), pp. 376-381. (Year: 2016).*

(Continued)

*Primary Examiner* — Siamak Harandi

(57) ABSTRACT

For processing a medical image, medical image data representing a medical image of at least a portion of a vertebral column is received. The medical image data is processed to determine a plurality of positions within the image. Each of the plurality of positions corresponds to a position relating to a vertebral bone within the vertebral column. Data representing the plurality of positions is processed to determine a degree of deformity of at least one vertebral bone within the vertebral column.

15 Claims, 2 Drawing Sheets

(56) References Cited

U.S. PATENT DOCUMENTS

2018/0005083 A1 1/2018 Georgescu et al.
2021/0097678 A1* 4/2021 Dutta .................. G06N 20/20

OTHER PUBLICATIONS

"COPD Genetic Epidemiology" Retrieved at http://www.copdgene.org/imaging. Date Accessed: Nov. 5, 2019.

Carberry, George A., et al. "Unreported vertebral body compression fractures at abdominal multidetector CT." Radiology 268.1 (2013): 120-126.

Deleskog, L., et al. "Vertebral fracture assessment by DXA is inferior to X-ray in clinical severe osteoporosis." Osteoporosis International 27.7 (2016): 2317-2326.

Diagnostic Imaging Pathways—Musculoskeletal/Trauma Pathways Retrieved at (https://www.facebook.com/pages/Diagnostic-Imaging-Pathways-Website/350279988477482) Date Accessed: Nov. 5, 2019.

Dismuke, Clara E., et al. "Clinical Factors and Expenditures Associated With ICD-9-CM Coded Trauma for the US Population: A Nationally Representative Study." Academic emergency medicine 24.4 (2017): 467-474.

World Health Organization. "Prevention and management of osteoporosis." World Health Organ Tech Rep Ser 921 (2003): 1-164.

Genant, Harry K., et al. "Vertebral fracture assessment using a semiquantitative technique." Journal of bone and mineral research 8.9 (1993): 1137-1148.

Roberts et al: "Quantitative Vertebral Fracture Detection on DXA Images Using Shape and Appearance Models"; Academic Radiology, Elsevier, Amsterdam, NL; vol. 14; No. 10; pp. 1166-1178; XP022338156; ISSN: 1076-6332, DOI: 10.1016/J.ACRA.2007.06.012; section 11 Data: DXA images; Sep. 20, 2007.

* cited by examiner

DETERMINATION OF A DEGREE OF DEFORMITY OF AT LEAST ONE VERTEBRAL BONE

RELATED CASE

This application claims the benefit of EP 18207641, filed on Nov. 21, 2018, which is hereby incorporated by reference in its entirety.

FIELD

The present embodiments relate to methods, apparatus and computer program products for processing a medical image.

BACKGROUND

Artificial Intelligence (AI) systems are increasingly being used to assist medical professionals, such as radiologists, to assess medical images. For example, a medical image of a chest contains a large number of anatomical structures (e.g. lungs, airways, heart, aorta, vertebrae and ribs) with each organ and pathology having a specific evaluation standard, which makes the examination of the medical image challenging. Accordingly, such an assessment of a medical image by a human assessor requires a high degree of training in order to provide an accurate evaluation of the medical image and to provide accurate findings.

Currently, compression fractures are mainly assessed with mid-sagittal X-ray images or dual energy X-ray absorptiometry (DXA) scans, and detection and quantification of a vertebral compression fracture is done through visual inspections according to methods such as the so-called Genant method. Computed tomography (CT) images of the chest are increasingly used for diagnosing a variety of medical conditions, but vertebral fractures are often underdiagnosed when interpreting CT scans, due to the increased workload on radiologists and the need for radiologists to focus their interpretation on other medical conditions such as lung cancer, chronic obstructive pulmonary disorder (COPD), and thoracic trauma. Less clinical attention is given to vertebral fractures possibly due to limited awareness of the clinical importance of such fractures and/or due to CT images being presented to radiologist in axial slices, in which perspective vertebral fractures can be difficult to detect. However, vertebral compression fractures are the most common osteoporosis-related fracture and osteoporosis is an increasing source of morbidity and mortality in older adults.

SUMMARY

These problems are solved or mitigated by the methods, by the data processing systems, and by the computer program product of the embodiments described herein.

The present embodiments relate in one aspect to a method of processing a medical image. The method includes:
receiving medical image data, the medical image data representing a medical image of at least a portion of a vertebral column;
processing the medical image data to determine a plurality of positions within the image, each of the plurality of positions corresponding to a position relating to a vertebral bone within the vertebral column; and
processing data representing the plurality of positions, to determine a degree of deformity of at least one vertebral bone within the vertebral column.

One embodiment relates in one aspect to a method wherein the plurality of positions each include a coordinate within the medical image, each coordinate representing a central point of a respective vertebral bone.

One embodiment relates in one aspect to a method wherein the plurality of positions includes positions representing a plurality of regions of interest, each region of interest bounding a respective vertebral bone.

One embodiment relates in one aspect to a method including processing data representing the plurality of positions to generate a model of the vertebral column.

One embodiment relates in one aspect to a method including determining the presence of one or more vertebral fractures on the basis of the determined degree of deformity.

One embodiment relates in one aspect to a method including:
determining, for each of the plurality of positions, a corresponding anatomical feature; and
assigning, to each of the regions of interest; a label representing the respective corresponding anatomical feature.

One embodiment relates in one aspect to a method including generating a mask including one or more regions of interest and representing the imaged vertebral column on the basis of the corresponding labels and centre coordinates.

One embodiment relates in one aspect to a method including:
segmenting each of the regions of interest of the image;
processing each of the regions of interest to determine one or more sagittal points for each of the corresponding vertebral bones; and
determining a Mahalanobis distance between each of the one or more sagittal points and the corresponding centre coordinates.

One embodiment relates in one aspect to a method including determining a mineral bone density value for each of the regions of interest, the mineral bone density values being determined based on Hounsfield Unit values within the respective regions of interest.

One embodiment relates in one aspect to a method including:
for each region of interest, determining an estimate of loss of height based on a comparison between a metric determined for a first region of region of interest and one or more adjacent regions of interest; and
determining the degree of deformity at least partly on the basis of the estimated loss of height.

One embodiment relates in one aspect to a wherein the estimate of loss of height includes an estimate of loss of height for anterior, mid and posterior portions of the corresponding vertebra.

One embodiment relates in one aspect to a method including determining a fracture classification and/or a severity of a fracture on the basis of the determined degree of deformity.

The embodiments relate in one aspect to a data processing system for processing medical images, the data processing system including a processor arranged to:
receive medical image data, the medical image data representing a medical image of at least a portion of a vertebral column;
process the medical image data to determine a plurality of positions within the image, each of the plurality of positions corresponding to a position relating to a vertebral bone within the vertebral column; and process data representing the plurality of positions, to determine a degree of deformity of at least one vertebral bone within the vertebral column.

One embodiment relates in one aspect to a data processing system wherein the processor is arranged to implement a trained deep image-to-image neural network to determine the plurality of positions, wherein the plurality of positions includes positions representing a plurality of regions of interest, each region of interest bounding a respective vertebral bone.

The embodiments relate in one aspect to a computer program, the computer program being loadable into a memory unit of a data processing system, including program code sections to make a data processing system execute the method according to an aspect when the computer program is executed in said data processing system.

The computer program product can be, for example, a computer program or include another element apart from the computer program. This other element can be hardware, for example a memory device, on which the computer program is stored, a hardware key for using the computer program and the like, and/or software, for example a documentation or a software key for using the computer program.

The image processing may be performed on any image data but in certain examples may be performed on medical image data representing a medical image. For example, the image may be acquired by a medical imaging device selected from the group consisting of an X-ray fluoroscopy device, a computed tomography device, a magnetic resonance imaging device, a molecular imaging device, a SPECT-device, a PET-device and combinations thereof. The medical imaging device can be, for example, a combination of an imaging modality and a therapy modality, in particular a radiation therapy modality.

Reference is made to the fact that the described methods and the described image processing apparatus are merely preferred example embodiments and that the invention can be varied by a person skilled in the art, without departing from the scope of the invention provided it is specified by the claims.

BRIEF DESCRIPTION OF THE DRAWINGS

The invention will be illustrated below with reference to the accompanying figures using example embodiments. The illustration in the figures is schematic and highly simplified and not necessarily to scale.

DETAILED DESCRIPTION OF THE PREFERRED EMBODIMENTS

Figure 1:
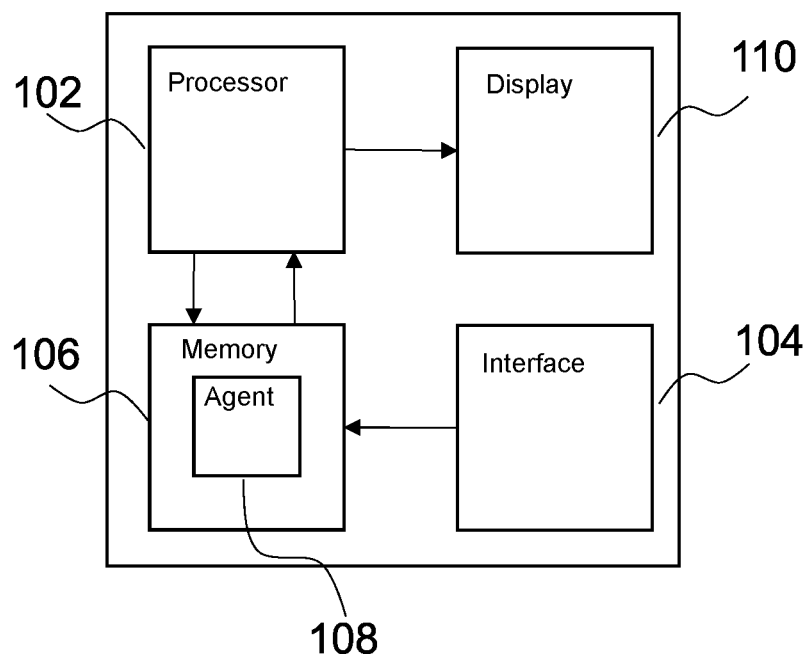
FIG. 1 is a schematic diagram of a data processing system according to one aspect.

FIG. 1 is a diagram illustrating a data processing system 100 according to an embodiment. The data processing system 100 includes a processor 102 configured to process a medical image, according to the methods described herein. The data processing system 100 may, for example, operate on a computing device, such as a workstation, desktop computer or laptop computer, or may operate on server, or may operate in a cloud environment.

For example, the processor 102 may be configured to perform image processing functions (i.e. by executing image processing algorithms, as described below) on medical image data. For example, the image may be acquired by a medical imaging device selected from the group consisting of an X-ray fluoroscopy device, a computed tomography device, a magnetic resonance imaging device, a molecular imaging device, a SPECT-device, a PET-device, and combinations thereof. The medical imaging device can be, for example, a combination of an imaging modality and a therapy modality, for example a radiation therapy modality. In some embodiments, the image may be retrieved from a picture archiving and communication system (PACS); for example, the image may be routed to the data processing system 100 using Digital Imaging and Communications in Medicine (DICOM) auto-routing. In some embodiments, the data processing system 100 may be part of an image acquisition system, such as a medical imaging device of the types described above. Alternatively, the data processing system 100 may be separate from the imaging device used to acquire an image and may be retrieved by the data processing system 100 or sent to the data processing system 100 via the communications interface 104.

The data processing system 100 also includes a communications interface 104 for receiving data, and a memory 106 for storing received data. The data received at the communications interface 104 may include image data. In some examples, the communications interface 104 may also be used to output a rendered result of the image processing performed by the data processing system 100. For example, the communications interface 104 may be used by the data processing system 100 to transfer image data to and/or from a Picture Archiving and Communications System (PACS).

The memory 106 may be arranged to store data in the form of a trained artificial intelligent agent, referred to hereinafter as an agent 108, that may be trained prior to installation and use of the data processing system 100 in an operation setting.

The agent 108 may be trained using a training set of examples to process medical image data to determine a degree of deformity of one or more vertebral bones within a medical image, for example, as described below in more detail.

The memory 106 may also store a computer program executable by the processor 102, to implement the agent 108 described above with reference to FIG. 1 and to perform the methods described herein such as, for example, the method described below with reference to FIG. 2. For example, the processor 102 may retrieve the agent 108 from the memory 106, apply inputs such as weightings to the agent 108, and obtain outputs from the agent 108.

The memory 106 may be any suitable non-transitory form of memory. For example, the memory 106 may include volatile memory, such as random-access memory (RAM) and/or nonvolatile memory such as read only memory (ROM) or flash memory. Furthermore, the memory 106 might include multiple, separate, memory devices and may include a combination of volatile and non-volatile memory. In some examples, certain components, such as the computer program and/or the agent, may be stored in one memory device, while other components may be stored in another memory device. In other examples, the memory may be an associative memory.

The processor 102 may be arranged to generate display information relating to the images and present the display information on a display 110.

Figure 2:
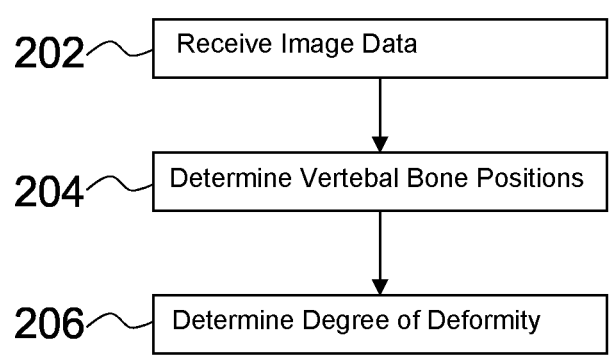
FIG. 2 is a simplified workflow diagram illustrating a method of processing image data for training an image processing system, according to one aspect.

FIG. 2 is a flow diagram depicting a method 200 of processing medical image data. For example, the method 200 may be implemented by the data processing system 100 described above with reference to FIG. 1.

At block 202, medical image data representing a medical image of at least a portion of a vertebral column is received. For example, as described above, the image data may be medical image data generated by, and received from, a medical imaging device such as an X-ray fluoroscopy device, a computed tomography device, a magnetic resonance imaging device, a molecular imaging device, a SPECT-device, a PET-device, and combinations thereof.

At block 204, the medical image data is processed to determine a plurality of positions within the image, each of the plurality of positions corresponding to a position relating to a vertebral bone within the vertebral column.

The plurality of positions may each include a coordinate within the medical image. For example, each coordinate represents a central point of a respective vertebral bone.

Additionally, or alternatively, the plurality of positions may include positions representing one or more regions of interest, each region of interest bounding a respective vertebral bone. In some embodiments, the data representing the plurality of regions of interest may be processed to generate a model of the vertebral column.

At block 206, data representing the plurality of positions is processed to determine a degree of deformity of at least one vertebral bone within the vertebral column.

For example, the degree of deformity may indicate the presence of one or more vertebral fractures.

In some embodiments, for each of the regions of interest, a corresponding anatomical feature may be determined. For each of the determined regions of interest, a label, representing a respective corresponding vertebral bone, may be assigned. For example, a label may be attached to each identified bone to identify that bone according to conventional anatomical standards.

In some embodiments, the data processing system 100 may generate a mask including the one or more regions of interest representing a model of the imaged vertebral column. The generation may be on the basis of the corresponding labels and/or the centre coordinates.

Figure 3:
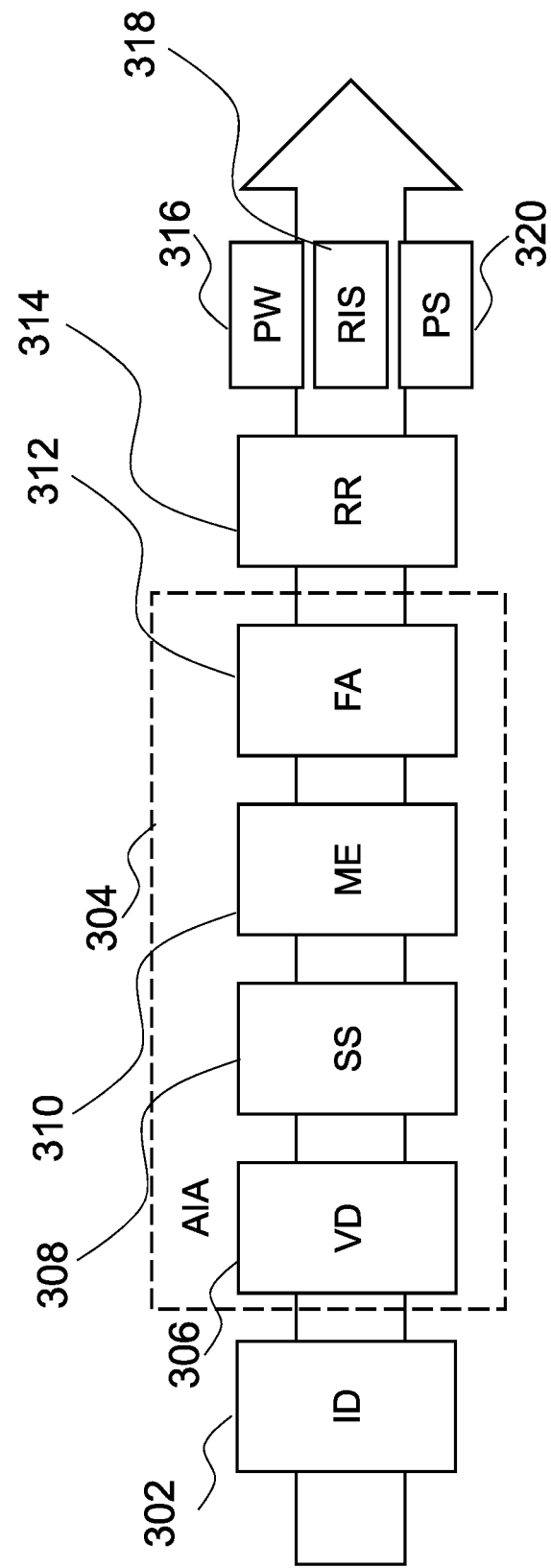
FIG. 3 is a schematic diagram illustrating an example workflow for performing vertebral compression fracture detection.

FIG. 3 is a schematic diagram of a workflow 300 for performing vertebral compression fracture detection.

Image data (ID) 302 is received by an artificial intelligence agent (AIA) 304, which may perform the function of the agent 108 described above with reference to FIG. 1. As explained above, the image data 302 is medical image data and may be, for example, CT image data relating to a chest of a human patient.

As shown in FIG. 3, the agent 304 may include multiple components including a vertebrae detection component (VD) 306, a spine segmentation component (SS) 308, a measurement extraction component 310, and a fracture assessment component (FA) 312.

The agent 304 receives the image data 302, which, as described above may be supplied by an imaging device or may be retrieved from a PACS storage facility.

The vertebrae detection component 306 receives as input the image data 302 and performs a processing operation to process the image data 302 to determine a plurality of positions within the image, each corresponding to a position relating to a vertebral bone within the vertebral column. For example, the vertebrae detection component 306 may implement a multiscale deep reinforcement learning agent trained to determine the coordinates of a central position of each vertebral bone in the image represented by the image data 302.

The vertebrae detection component 306 outputs the plurality of positions. For example, the vertebrae detection component 306 may output a list of coordinates corresponding to each of the vertebral bones in the image. In some embodiments, the vertebrae detection component 306 may also output a label corresponding to each of the vertebral bones, which identifies the respective bone. In some embodiments, the vertebrae detection component 306 may additionally, or alternatively, output a plurality of positions forming a region of interest in the form of a bounding box around each vertebral bone.

The output from the vertebrae detection component 306 is received as input to the spine segmentation component 308. The spine segmentation component 308 performs a processing operation to process the plurality of positions to generate a multilabel mask representing a model of the spine, in which each of the vertebral bones is represented in the mask and labelled. In some embodiments, the spine segmentation component 308 crops a region of interest around each detected vertebral bone; the region of interest may include the vertebral bone and surrounding portions of the image (to provide context). The spine segmentation component 308 may then segment the vertebral bones in each region of interest and merge the segmented vertebral bones into a global mask.

In some embodiments, the spine segmentation component 308 may use a trained deep image-to-image (DI2I) network to perform the segmentation. The DI2I network is a multilayer convolutional neural network (CNN) trained to perform vertebral body segmentation of a region of interest of a 3D medical image. The DI2I network generates a probability map mapping, for each voxel, the probability of that voxel being part of either, the central vertebral body, the top vertebral bodies, the bottom vertebral bodies or outside a vertebral body. From the probability map, a mask can be derived in which each voxel is classified according to the highest probability.

In some embodiments, the structure of the DI2I network may be arranged symmetrically as a convolutional encoder-decoder. Each of the blocks of the DI2I network may represent one or more layers of the network. The blocks of the DI2I network may include, for example, three-dimensional convolutional and/or transposed convolutional layers.

The DI2I network is trained prior to installation of the agent 304 in an operational setting by providing, to the agent 304, training data including training images and corresponding ground truth data representing vertebral body segmentation masks for the training images. For example, the DI2I network may be trained with a Leaky rectifier linear unit (Leaky ReLU) providing activation functions.

Each training image is a 3D medical image. In some embodiments, the training images may be three-dimensional computed tomography (CT) volumes. In other embodiments, the training images may be contrast-enhanced CT volumes. In other embodiments, the training images may be three-dimensional magnetic resonance (MR) images or three-dimensional medical images acquired using other medical imaging modalities, such as ultrasound, positron emission tomography (PET), etc.

The ground truth vertebral body segmentation mask for each training image can be implemented as a three-dimensional multilabel mask image of the same grid size as the training image in which the central vertebral body voxels have an intensity value of 1, top vertebral bodies voxels have an intensity value of 2, bottom vertebral bodies voxels have an intensity value of 3, and voxels outside the vertebral bodies boundary have an intensity value of 0. The ground truth vertebral body segmentation masks may, for example, be manually generated by annotating vertebral body boundaries in the training images.

In other embodiments, the spine segmentation component 308 may be implemented using an adversarial deep image-to-image network.

The multilabel mask of the spine output by the spine segmentation component 308 is received as input by the measurement extraction module 310. For each detected vertebral bone, the measurement extraction component 310 extracts the segmented vertebral body and extracts one or more sagittal points for the corresponding vertebral bone. In some embodiments, the measurement extraction component 310 extracts six sagittal points, which is the number of sagittal points required by the Genant method. The measurement extraction component 310 then determines a Mahalanobis distance between each of the one or more sagittal points and the corresponding centre coordinates of each vertebral bone. In some embodiments, the measurement extraction component 310 determines a mineral bone density value for each of the vertebral bones within the image. For example, the mineral bone density values may be determined based on Hounsfield Units values of voxels within the anatomical structure (i.e. vertebral bone) of interest. The measurement extraction component 310 may provide a standardized and reproducible approach to quantify and compare vertebral compression fractures.

The measurements extracted by the measurement extraction module 310 are received as input by the fracture assessment component 312. The fracture assessment component 312 performs a processing operation to process the input image data 302 and the measurements extracted for each vertebral bone by the measurement extraction component 310 to determine an estimate of loss of height for the corresponding vertebral bone. For example, the loss of height may be determined based on a comparison between a metric or measurement determined for a first region of interest (corresponding to a first vertebral bone) specified in the mask or model and one or more adjacent regions of interest (corresponding to one or more adjacent vertebral bones) specified in the mask or model. In some embodiments, a loss of height may be determined, for example, at anterior, mid, and posterior portions of the corresponding vertebra.

The fracture assessment component 312 may then determine a degree of deformity based on the estimated loss of height and/or the comparison between adjacent vertebral bones and, based on the determined degree of deformity, determine a fracture classification and/or degree of severity of a fracture; for example, the fracture assessment component 312 may assign a grade for severity and deformity according to the standards prescribed by the Genant method.

The output from the fracture assessment component 312 is processed by a result rendering component 314, which processes the output into one or more data formats suitable for storage and/or presentation to a user. In some embodiments, the result rendering component 314 may then transfer the processed output to one or more of: a PACS workstation (PW) 316; a radiological information system (RIS) 318; and a PACS storage (PS) facility 320. In some embodiments, the PACS workstation 316 and/or the radiological information system 318 may include a display such as the display 110 described above with reference to FIG. 1, and the result rendering component 314 may generate display data to be presented on the display 110. For example, the result rendering component 314 may prepopulate a report with findings based on the output from the fracture assessment component 312 for display on the display 110. In some embodiments, the result rendering component 314 may be arranged to overlay the results from the fracture assessment component 312 on the medical image represented by the image data 302 (such as a CT scan) and for presentation on the PACS workstation 316 or storage in the PACS storage facility 320, which may remove the need for a user to switch workstation or application to view the results generated by the fracture assessment component 312.

The above-described embodiments may provide improved detection and assessment of vertebral fractures over conventional methods. For example, the above-described embodiments, may provide a reduction in the time required to assess and interpret chest CT scans, allowing the radiologist to spend more time on advanced analysis. Interaction between the agent 304 and the PACS workstation 316, the radiological information system (RIS) 318, and the PACS storage facility 320 (i.e. existing PACS and RIS infrastructure) may improve diagnostic efficiency as well as improve the quality of the assessment of vertebral fractures. In particular, difficulties in using CT scans for the assessment of vertebral fractures may be solved or mitigated, and the underdiagnosis of vertebral compression fractures may be reduced.

While the invention has been illustrated and described in detail with the help of a preferred embodiment, the invention is not limited to the disclosed examples. Other variations can be deducted by those skilled in the art without leaving the scope of protection of the claimed invention.

The invention claimed is:

1. A method of determining a degree of deformity of at least one vertebral bone, the method comprising:
    receiving medical image data, the medical image data representing a medical image of at least a portion of a vertebral column;
    determining, from the medical image data, a plurality of positions, each of the plurality of positions corresponding to a position relating to a vertebral bone within the vertebral column;
    generating, from at least the plurality of positions, a multilabel mask representing a model of the vertebral column, the model including a region of interest around each of the plurality of vertebral bones;
    extracting one or more vertebrae measurements from the multilabel mask and the plurality of positions; and
    determining, from the extracted one or more vertebrae measurements, the degree of deformity of the at least one vertebral bone within the vertebral column.

2. The method according to claim 1, wherein the plurality of positions each comprises a coordinate within the medical image, each coordinate representing a central point of the respective vertebral bone.

3. The method according to claim 1, further comprising determining the presence of one or more vertebral fractures on the basis of the determined degree of deformity.

4. The method according to claim 1, wherein generating the multilabel mask further comprises:
    determining, for each of the plurality of positions, a corresponding anatomical feature; and
    assigning, to each of the regions of interest, a label representing the respective corresponding anatomical feature.

5. The method according to claim 1, wherein extracting one or more vertebrae measurements comprises:
   determining one or more sagittal points for each of vertebral bones; and
   determining a Mahalanobis distance between each of the one or more sagittal points and corresponding center coordinates of each of the vertebral bones.

6. The method according to claim 1, wherein extracting one or more vertebrae measurements comprises:
   determining a mineral bone density value for each of the regions of interest, the mineral bone density values being determined based on Hounsfield Unit values within the respective regions of interest.

7. The method according to claim 1, wherein determining the degree of deformity comprises:
   for each region of interest, determining an estimate of loss of height based on a comparison between the one or more vertebrae measurements a first region of region of interest and one or more adjacent regions of interest; and
   determining the degree of deformity at least partly on the basis of the estimated loss of height.

8. The method according to claim 7, wherein the estimate of loss of height comprises an estimate of loss of height for anterior, mid, and posterior portions of the corresponding vertebra.

9. The method according to claim 1, further comprising determining a fracture classification or a severity of a fracture on the basis of the determined degree of deformity.

10. A data processing system for determining a degree of deformity of at least one vertebral bone, the data processing system comprising:
    a processor configured to:
    receive medical image data, the medical image data representing a medical image of at least a portion of a vertebral column;
    process the medical image data to determine a plurality of positions within the image, each of the plurality of positions corresponding to a position relating to a vertebral bone within the vertebral column;
    generate, from at least the plurality of positions, a multilabel mask representing a model of the vertebral column, the model including a region of interest around each of the plurality of vertebral bones;
    extract one or more vertebrae measurements from the multilabel mask and the plurality of positions; and
    process the one or more vertebrae measurements to determine a degree of deformity of at least one vertebral bone within the vertebral column.

11. The data processing system according to claim 10, wherein the processor is configured to implement a trained deep image-to-image neural network to determine the plurality of positions.

12. The data processing system according to claim 10, wherein the processor is configured to:
    determine, for each of the plurality of positions, a corresponding anatomical feature; and
    assign, to each of the regions of interest, a label in the multilabel mask representing the respective corresponding anatomical feature.

13. The data processing system according to claim 10, wherein the processor is configured to:
    process each of the regions of interest to determine one or more sagittal points for each of the corresponding vertebral bones; and
    determine a Mahalanobis distance between each of the one or more sagittal points and the corresponding center coordinates.

14. The data processing system according to claim 10, wherein the processor is configured to determine a mineral bone density value for each of the regions of interest, the mineral bone density values being determined based on Hounsfield Unit values within the respective regions of interest.

15. A non-transitory computer readable storage medium comprising a computer program, the computer program being executable by a processor, the computer program including program code for:
    receiving medical image data, the medical image data representing a medical image of at least a portion of a vertebral column;
    determining, from processing the medical image data, a plurality of positions within the image, each of the plurality of positions corresponding to a position relating to a vertebral bone within the vertebral column;
    generating, from at least the plurality of positions, a multilabel mask representing a model of the vertebral column, the model including a region of interest around each of the plurality of vertebral bones;
    determining one or more sagittal points for each of the corresponding vertebral bones;
    determining a Mahalanobis distance between each of the one or more sagittal points and corresponding center coordinates of each of the plurality of vertebral bones; and
    determining, from at least the Mahalanobis distances, a degree of deformity of at least one vertebral bone within the vertebral column.

* * * * *